US011224444B2

(12) United States Patent
Hafez et al.

(10) Patent No.: US 11,224,444 B2
(45) Date of Patent: Jan. 18, 2022

(54) PATIENT SPECIFIC TEMPLATE AND METHOD FOR PARTIAL KNEE REPLACEMENT

(71) Applicants: Mahmoud Alm El Din Hafez, Giza (EG); Ahmed Abdel Moghny Salem, Giza (EG)

(72) Inventors: Mahmoud Alm El Din Hafez, Giza (EG); Ahmed Abdel Moghny Salem, Giza (EG)

(73) Assignee: Mahmoud Alm El Din Hafez, Giza (EG)

( * ) Notice: Subject to any disclaimer, the term of this patent is extended or adjusted under 35 U.S.C. 154(b) by 75 days.

(21) Appl. No.: 16/463,939

(22) PCT Filed: Nov. 21, 2017

(86) PCT No.: PCT/EG2017/000030
§ 371 (c)(1),
(2) Date: May 24, 2019

(87) PCT Pub. No.: WO2018/095499
PCT Pub. Date: May 31, 2018

(65) Prior Publication Data
US 2020/0197023 A1    Jun. 25, 2020

(30) Foreign Application Priority Data

Nov. 24, 2016 (EG) ................................ 2016111920

(51) Int. Cl.
*A61B 17/58* (2006.01)
*A61B 17/60* (2006.01)
(Continued)

(52) U.S. Cl.
CPC .......... *A61B 17/155* (2013.01); *A61B 17/157* (2013.01); *A61B 17/1764* (2013.01); *A61F 2/30942* (2013.01); *A61B 2017/568* (2013.01)

(58) Field of Classification Search
CPC combination set(s) only.
See application file for complete search history.

(56) References Cited

U.S. PATENT DOCUMENTS

2014/0107655 A1* 4/2014 Song ................. A61B 17/1764
606/88
2015/0190144 A1* 7/2015 Kennedy ............. A61B 17/157
606/88

FOREIGN PATENT DOCUMENTS

EP         3009110        5/2012
WO       2012058355       5/2012
(Continued)

*Primary Examiner* — Sameh R Boles
(74) *Attorney, Agent, or Firm* — Dickinson Wright PLLC; Andrew D. Dorisio

(57) ABSTRACT

This invention relates to a surgical device for preparing the knee joint of a patient undergoing to partial knee replacement. The device is patient specific and has information about implant size, alignment and bone cut.
This device consists of two parts, one is related to femoral template and the other one is related to tibial template. The femoral template positioned to a predefined location on the femur bone based on virtual planning of the surgery on specific software using 3D imaging. The femoral template allows to perform the posterior distal cut, drill and detect the location of the two holes relevant to the distal cut and implant pegs, while the tibial template allows the surgeon to make the tibial horizontal and vertical cuts; beside that, it has double slots which allows the surgeon to make extra bone removal if needed or when deciding to use larger size of polyethylene insert.

11 Claims, 25 Drawing Sheets

(51) Int. Cl.
*A61F 2/00* (2006.01)
*A61B 17/15* (2006.01)
*A61B 17/17* (2006.01)
*A61F 2/30* (2006.01)
*A61B 17/56* (2006.01)

(56) References Cited

FOREIGN PATENT DOCUMENTS

| WO | WO 12058355 A1 | 5/2012 |
| WO | 2016124209 | 8/2016 |
| WO | WO 16124209 A2 | 8/2016 |

* cited by examiner

PATIENT SPECIFIC TEMPLATE AND METHOD FOR PARTIAL KNEE REPLACEMENT

TECHNICAL FIELD

The invention is a device for preparing a knee joint for a prosthesis in a patient undergoing uni-compartmental knee arthroplasty (UKA) surgery for any knee implant regardless of its manufacturer. The device is patient specific and guides the surgeons to perform the reference cuts.

Problems with the Current Art

Uni-compartmental knee replacement surgeries are currently well known and many surgeons rely on it as a safe and easy alternative to the total knee replacement. It also enables the patient to exercise his normal life better than the patient who is undergoing total knee replacement. The UKA gives the patient a chance for wide range of motion with ability to run and loading the knee joint more than other patients who undergo total knee replacement.

Using X-ray for surgical planning may result in lower percentage of success due to the lack of accuracy in positioning the implant in the correct location over the bone, in addition to incorrect alignment, sizing of the implant and polyethylene part sizing.

On the other hand, the conventional surgical instruments used in the UKA are complex, large in number and require considerable time for sterilization and a skilled surgeon to deal with this large number of instruments. The large number of steps used in UKA needs a long learning curve and accumulated experiences for many years, which decrease the chance for young and junior surgeons to easily improve their knowledge about this technique.

Due to the large number of boxes of the surgical instruments, and the limitation of detecting the implant size before surgery, therefore, the transportation of these surgical kits is not an easy action, especially in developing countries that have limited budget for purchasing large number of kits to overcome this problem. This situation will lead to increasing the waiting list in the hospitals for the UKA.

BACKGROUND ART

Patient Specific Instruments (PSI) for knee arthroplasty is a famous technique. It involves image-based preoperative planning, followed by the production of templates that match the surface geometry of the patient's bony structures. The planning method depends on 3D imaging scanning (CT or MRI).

In the background art, in the field of the uni-compartmental knee replacement, the conventional instruments are the player and there is no background art dealing with the patient specific instruments in performing the uni-compartmental knee replacement surgeries.

The background art of the patient specific instruments are used in anther application as total knee replacement in human and small animals (WO 2016/124209 A2 and EP 3009110 A1). The function of these patient specific instruments is a cutting guide and pin locator to locate the proper position of the conventional cutting guides over the bone.

On the other hand, this invention is a state of the art for patient-specific application in the uni-compartmental knee replacement. It includes a cutting slots performing the vertical cutting and horizontal cutting of the tibia bone and characterized by a positioning arms provides a correct and safe method to position the device over the bone.

DISCLOSURE OF INVENTION

The invention is a device for preparing a knee joint for a prosthesis in a patient undergoing UKA surgery for any knee implant regardless of its manufacturer. The device is suitable to be used for all on-shelf implants and all patient specific implants. This device can be used for mobile and fixed bearing implants The device is a cutting guide used to perform bone resection. The device consists of two parts: one for the femoral component (FIG. 1-1, label 1) and the other for the tibial component (FIG. 3, label 11). The device contains cutting slots and holes to perform the bone resection (FIG. 2, labels 2, 3 and 4) and (FIG. 4, labels 12, 13 and 14). The device contains locating arms and fixation holes (FIG. 2, labels 5 and 7) and (FIG. 4, labels 15, 16 and 17). The tibial component has fixation holes in two types: parallel fixation holes (FIG. 4, labels 17) and inclined fixation holes (FIG. 4, labels 15 and 16) to provide a secure positing of the tibial component over the tibia bone.

The femoral component has parallel fixation holes in different diameters which allow the surgeon a variety of fixation points according to the anatomical shape of the femur bone (FIG. 2, labels 5 and 7).

The femoral component has locating arms (FIG. 2, labels 8, 9 and 10) which increase the movement constraints and decrease the degrees of freedom for the device over the bone. This feature helps the inexperienced surgeons to position and orient the device over the bone in easy and correct way.

The improvement in this invention over the background art are the double cutting slots (label 12 and 14) which locating in the tibial component and allow the surgeons to get a chance for cutting more bone from the tibia bone if needed and in case of incorrect sizing of the tibial implant. The vertical cutting slot (label 13) is novel step over the conventional instrument because the conventional instruments does not have any cutting block performing the tibial vertical cutting by means the surgeon do this cut manually in case of using the conventional instruments, but this invention provides a vertical cutting slot to solve this problem and allows the surgeon to perform this action in a correct and safe way. The other improvement of this invention is the inclined fixation holes in the tibial component (label 15 and 16) which overcome the problem of mis-positioning and mis-alignment of the patient specific instruments in the background art. The parallel fixation holes (label 17) help the surgeons to uninstall the device and installing the conventional instruments in the same position decided by the preoperative surgery planning on the relevant software.

In the femoral component, the improvement in this invention over the background art is positioning arms (label 6, 8, 9 and 10) which relies on a landmark on the femur bone in a novel technique based on the anatomical shape of the femur bone. These arms allow the surgeons, especially the inexperienced surgeon to locate and position the device over the bone in a certain position decided by the preoperative surgery planning on the relevant software. In addition, the surgeon use this feature instead of the intramedullary rod in the conventional instruments, the intramedullary rod cannot be using for the patients who have a femoral bowing, fat embolism and/or severe deformity.

This device is a patient-specific surgical template used for performing reference cuts for knee joint in patients undergoing urn-compartmental knee replacement. The device consists of two parts: a femoral part and a tibial part, both include locating arms, fixation holes and cutting slots. The two parts have built-in information about sizing, alignment and bone cutting; this information is applied to the template from the preoperative planning of the surgery. The preoperative planning is comprised of 3D evaluation of the anatomy and pathology of the knee joint and identification of landmarks.

While the conventional instrumentation is very complex and has a long learning curve, the device is used to assist the surgeons to perform the surgery of uni-compartmental knee replacement in a few steps regardless to the experience of the surgeon.

The formal component is configured to perform the posterior cut and drilling the two main holes for the fixation of femoral component over the femur bone (FIG. 2, labels 2, 3 and 4) and (FIGS. 5, 6, 7, 8 and 9). The tibial component allows the surgeon to make the horizontal and vertical tibial cuts. The tibial component has a creative and unique design for the cutting plane with double slots, which allows the surgeon to make extra, bone removing if needed (FIG. 1, labels 12, 13 and 11) and (FIGS. 10, 11, 12, 13 and 11). Also, both parts also have extensions along the cutting slots surface to guide the surgeon to the correct slope and inclination of the saw blade when cutting the bone.

The device is designed to allow surface matching of the device for both formal and tibial parts to rely on protruding locating probes and arms that match bony surfaces in cartilage-free area(s). In addition, it is characterized by fixations holes in oblique and parallel directions to securely fix the instruments over the bone (FIGS. 5, 6, 7, 8, 9, 10, 11, 12, 13, 14).

The device provides planning and implantation of surgery based on reference cuts. The definition of reference cuts are posterior femoral cut, tibial cut and vertical cut. All of these reference cuts are standard parameters for uni-compartmental knee replacement regardless of the implant used (FIGS. 8, 9, 12, 13 and 14).

The interior surface of the femoral and tibial component has formation in identical shape to the outer surface of femoral and tibial bone, respectively. The formation of the interior surface is the main feature of the device, because it assists the surgeon to locate and align the device over the bone (FIGS. 15 and 16).

An additional planning method is used based on 2D data and the main dimensions of the implant as anteroposterior and mediolateral dimensions and angles of posterior femoral cut and tibial posterior slope. All of these data allow the surgeon to detect the level of resection for both femoral and tibial components. The cuts are based on 2D data of implant; this means that for any future implant we need only the 2D data of the implant which are available for all users and surgeons rather than the 3D data which are confidential and property of implants' companies.

Our method gives the surgeon a flexibility to change the planned size of implant according to intraoperative conditions. For example, decreasing the size of the femur to increase the flexion gap and vice versa. The same change for sizing of the tibia according to matching and rotation to overcome the overhang or undercutting. In addition, this device allows extra cutting for the tibia using conventional instruments, where the cutting block is positioned on the cut surface to allow the cut of 2 or 3 mm of bone parallel to the initial cut surface that was done by the tibial template (FIG. 4, labels 12 and 13).

Figure 1:
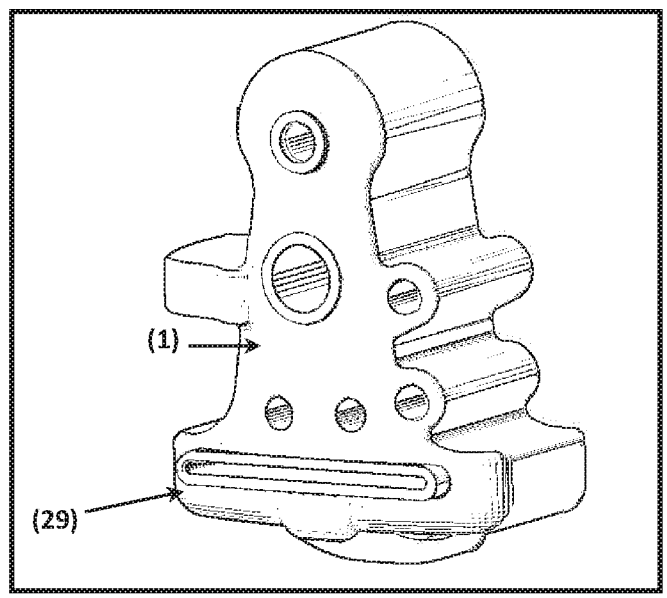
FIG. 1: Isometric views of the femoral template, showing the design of the template from the front side (FIG. 1-1) and from the back FIG. (1-2). FIG. (1-2) shows the posterior cutting slot (2), femoral component fixation holes ((3) and (4)), fixation holes (5), fixation legs ((6) and (7)), the alignment legs (8), (9) and (10)) and the extension along the cutting slot (29).
Figures 1, 2:
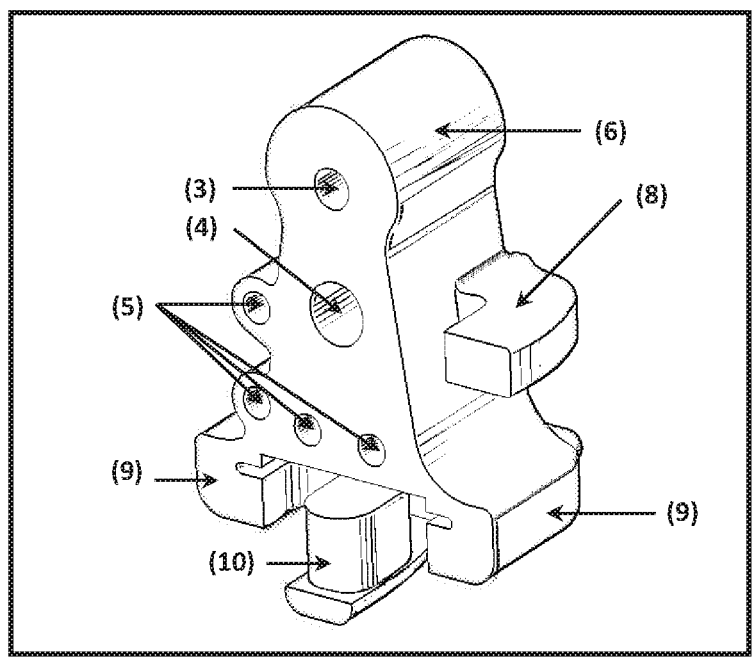
FIG. 2: 2D views of the femoral template, showing the design of the template from the front side (FIG. 2-1) and from the back FIG. (2-2). FIG. (2-1) shows the posterior cutting slot (2), femoral component fixation holes ((3) and (4)), fixation holes (5), fixation legs ((6) and (7)) and the alignment legs ((8), (9) and (10)).
Figures 1, 2:
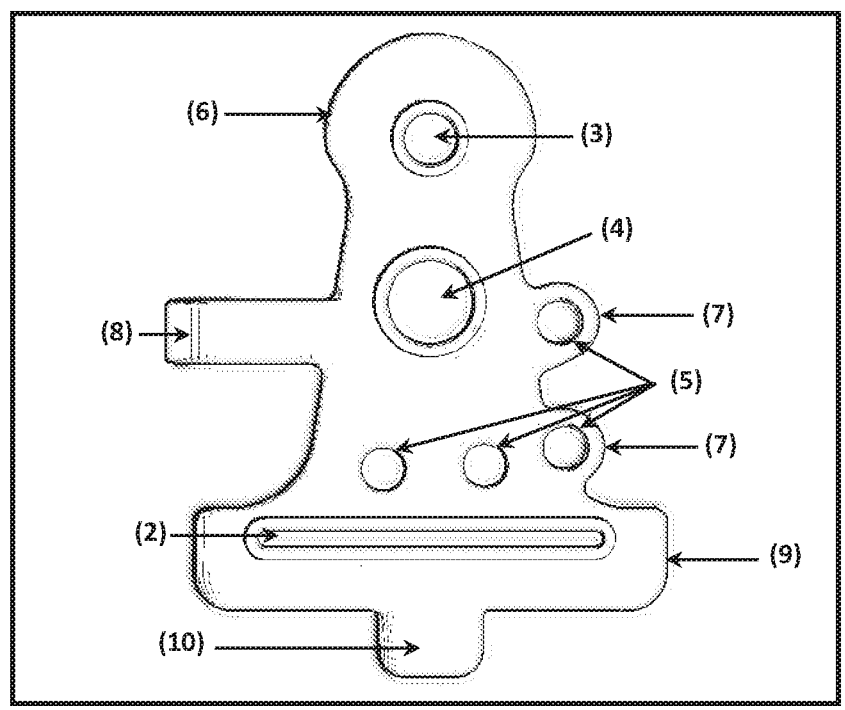
Figure 2:
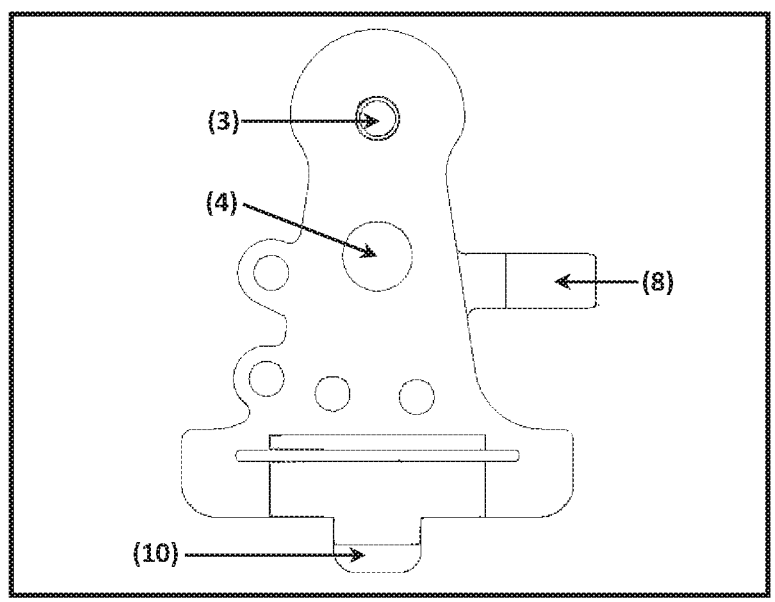
Figures 1, 3:
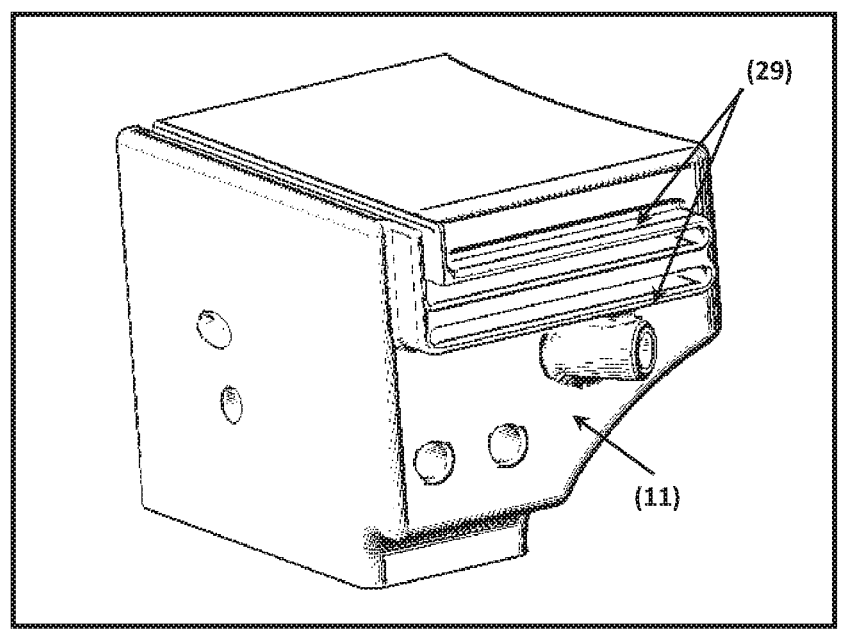
FIG. 3: Isometric views of the tibial template, showing the design of the template from the medial view (FIG. 3-1) and from the lateral view (3-2) and the extension along the cutting slot (29).
Figures 2, 3:
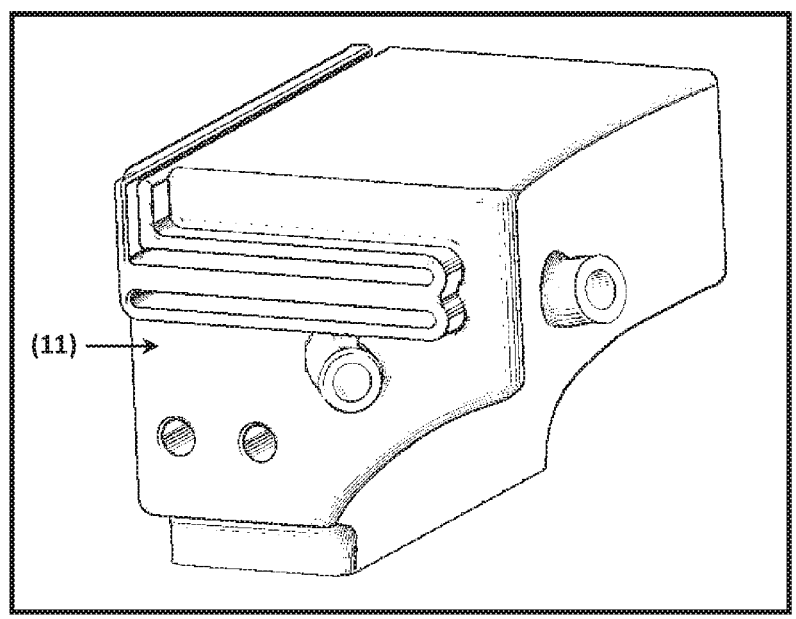
Figures 1, 4:
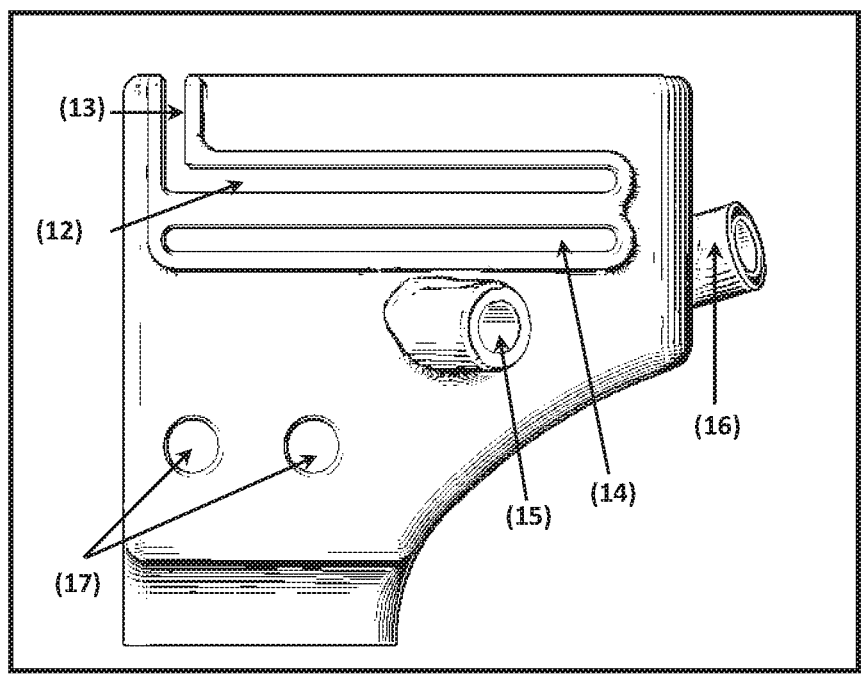
FIG. 4: 2D views of the femoral template, showing the design of the template from the front side (FIG. 4-1) and from the back FIG. (4-2). FIG. (4-1) shows the vertical cutting slot (13), the primary cutting slot (12), the secondary cutting slot (14) and the fixation holes ((15), (16) and (17)).
Figures 2, 4:
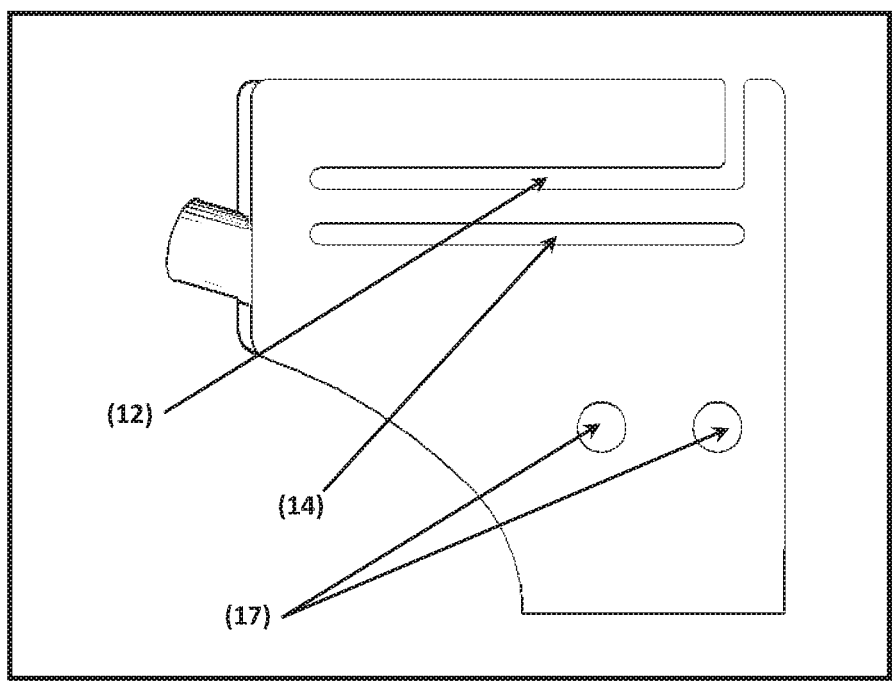
Figure 5:
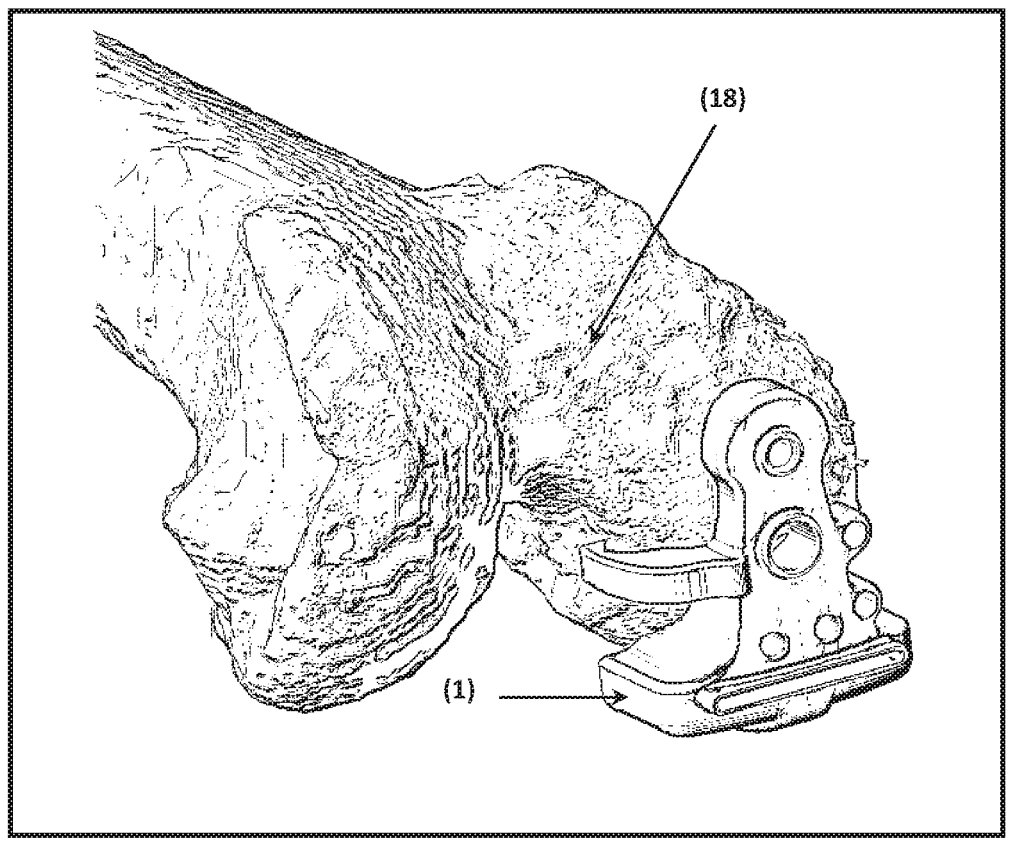
FIG. 5: shows the femoral template over the bone (medial view).
Figure 6:
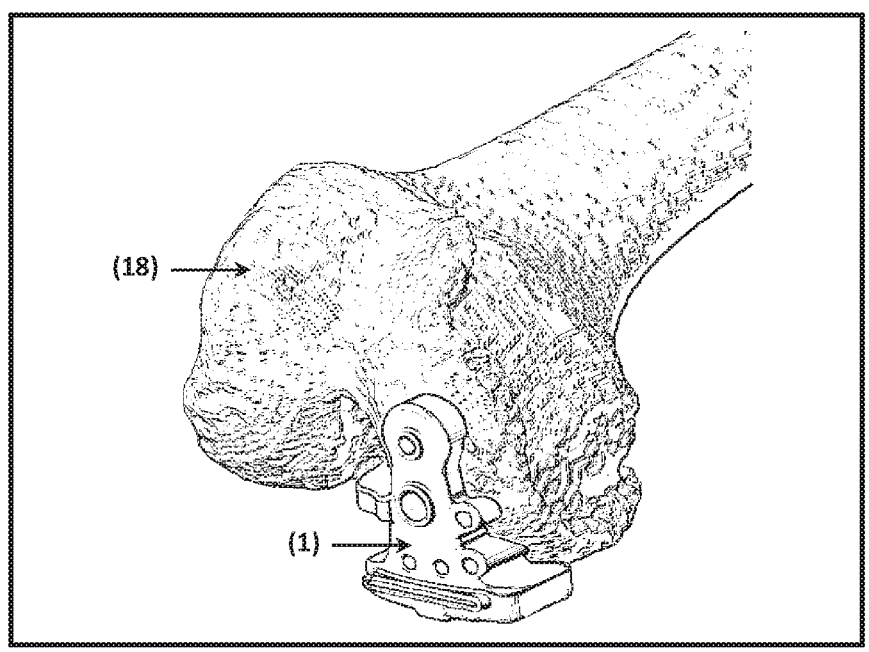
FIG. 6: shows the femoral template over the bone (lateral view).
Figures 1, 7:
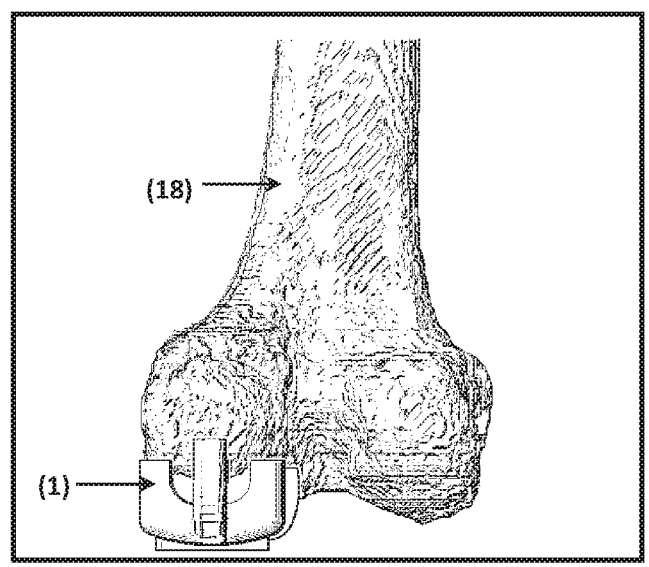
FIG. 7: 2D views of the femoral template over the bone. FIG. (7-1) shows a back view of the femoral template over the bone, FIG. (7-2) shows a side view of the femoral template over the bone, FIG. (7-3) shows a bottom view of the femoral template over the bone.
Figures 2, 7:
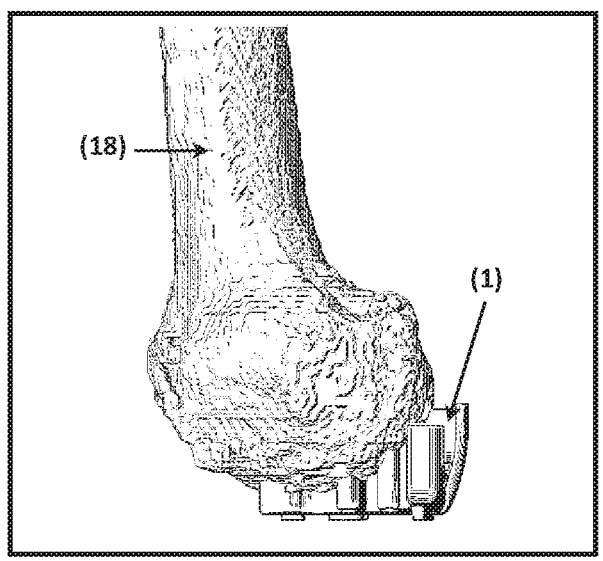
Figures 3, 7:
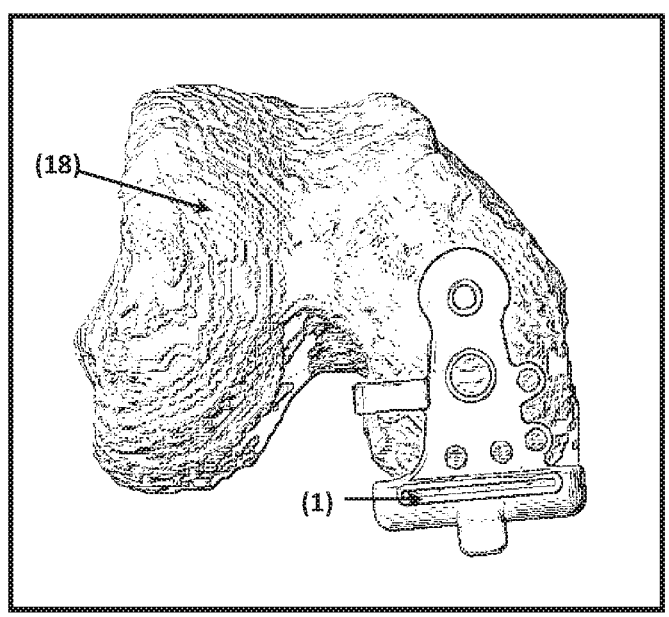
Figure 8:
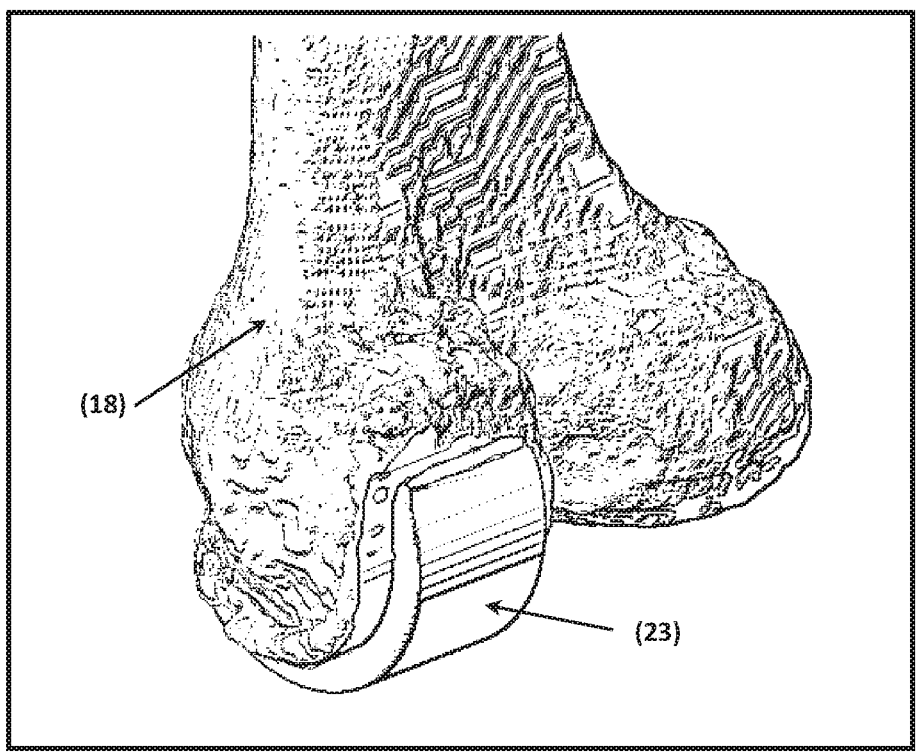
FIG. 8: Isometric view of the femoral component (prosthesis) (23) over the bone (18) after performing the surgery.
Figures 1, 9:
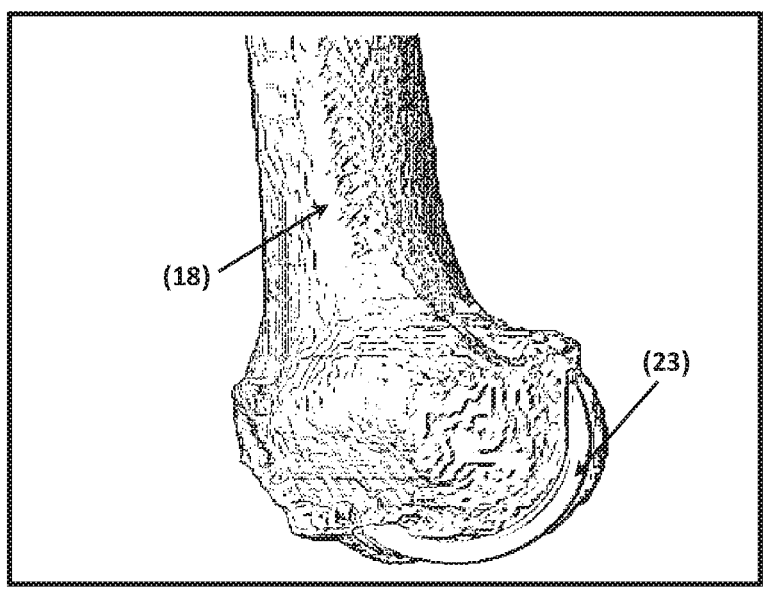
FIG. 9: 2D views of the femoral component (prosthesis) (23) over the bone (18) after performing the surgery. FIG. (9-1) shows a side view of the femoral component over the bone, FIG. (9-2) shows a bottom view of the femoral component over the bone.
Figures 2, 9:
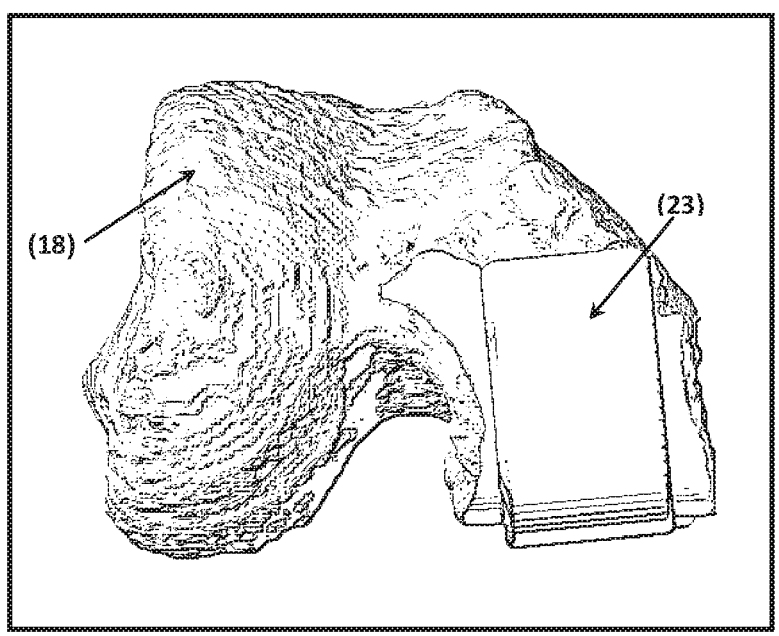
Figure 10:
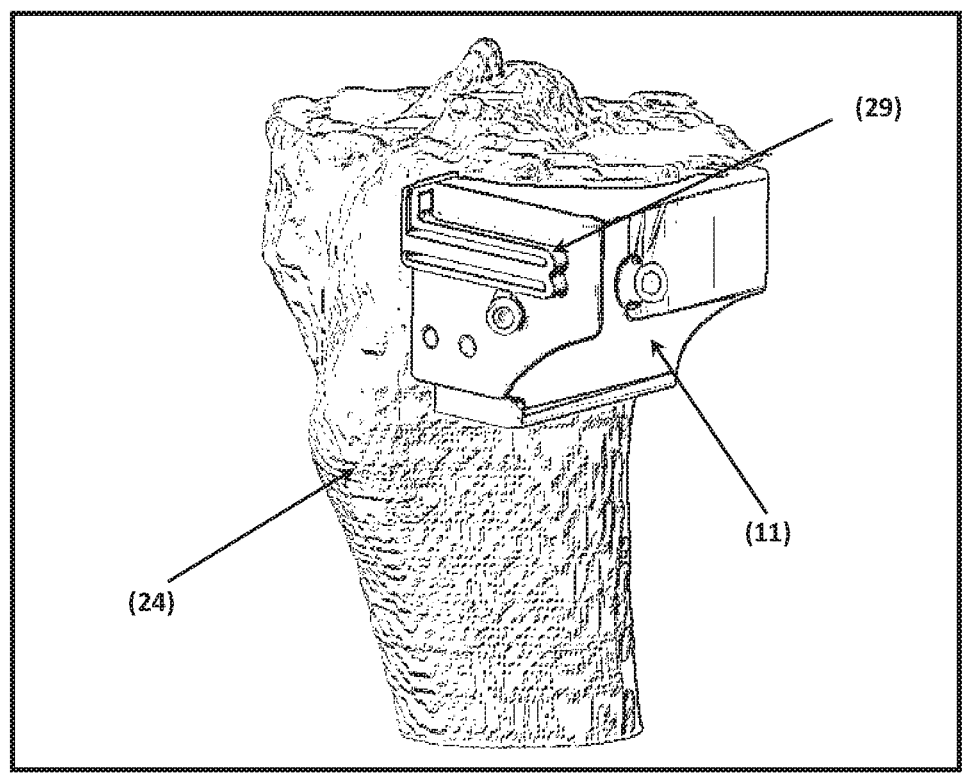
FIG. 10: shows the tibial template (11) over the tibia bone (24) (lateral view).
Figures 1, 11:
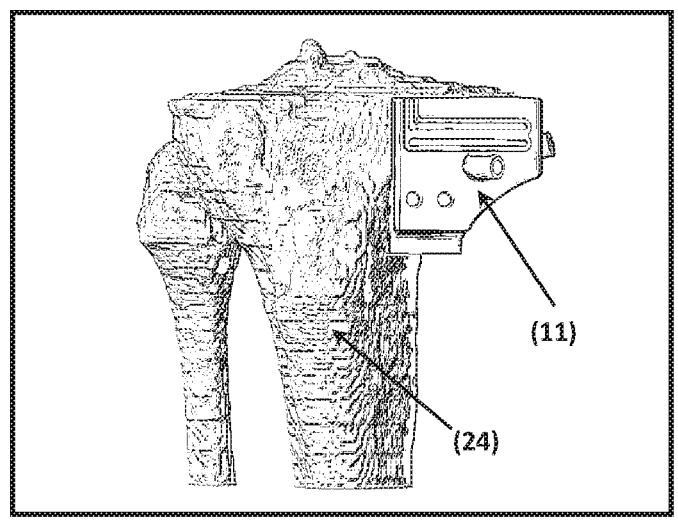
FIG. 11: 2D views of the tibial template over the bone. FIG. (11-1) shows a front view of the tibial template over the bone, FIG. (11-2) shows a side view of the tibial template over the bone, FIG. (11-3) shows a top view of the tibial template over the bone.
Figures 2, 11:
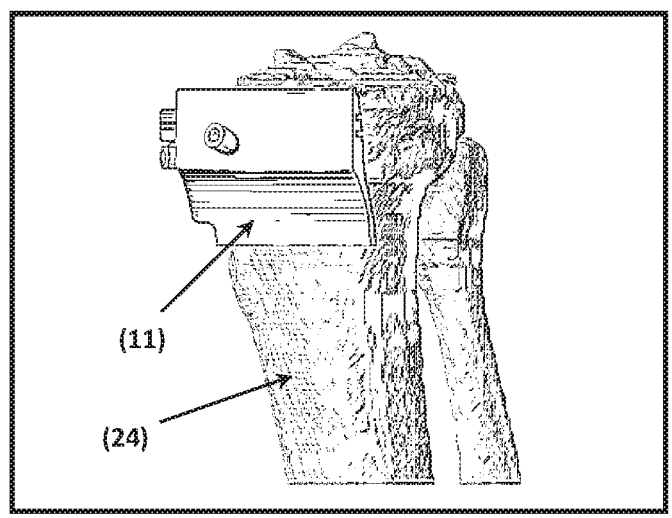
Figures 3, 11:
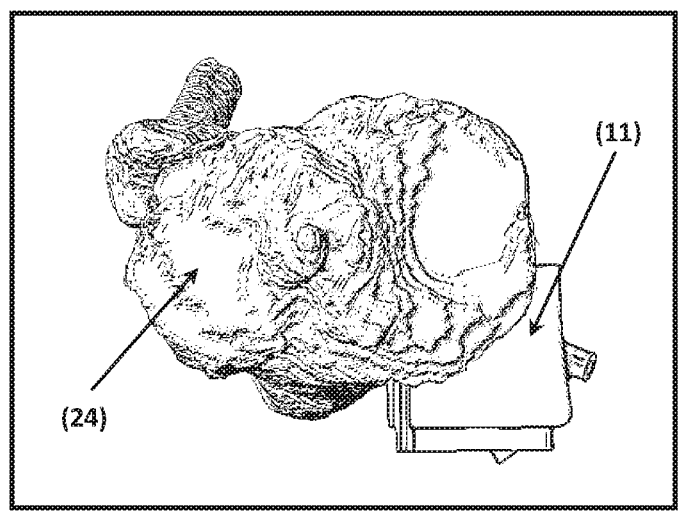
Figure 12:
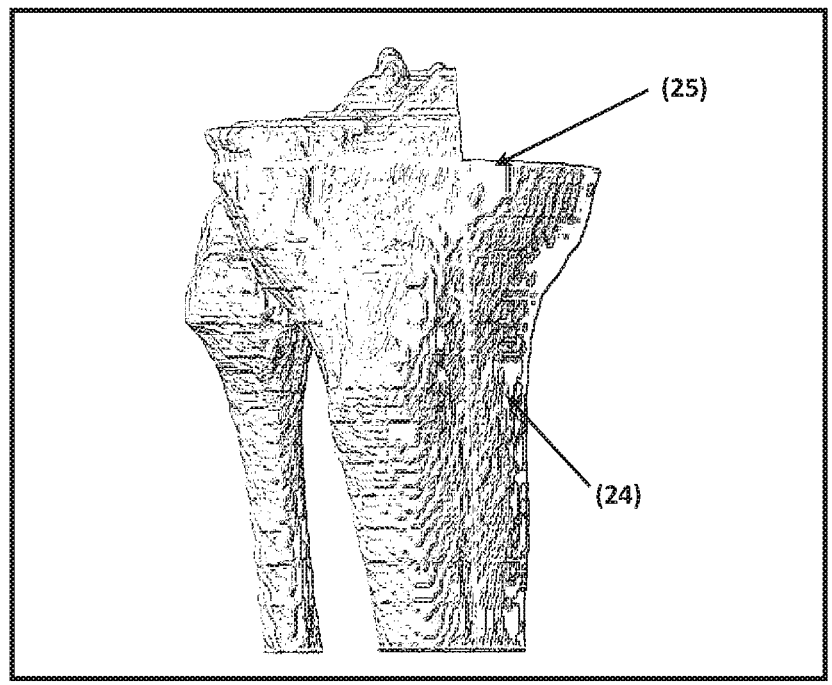
FIG. 12: shows the tibia bone after performing the tibial cut and vertical cut.
Figure 13:
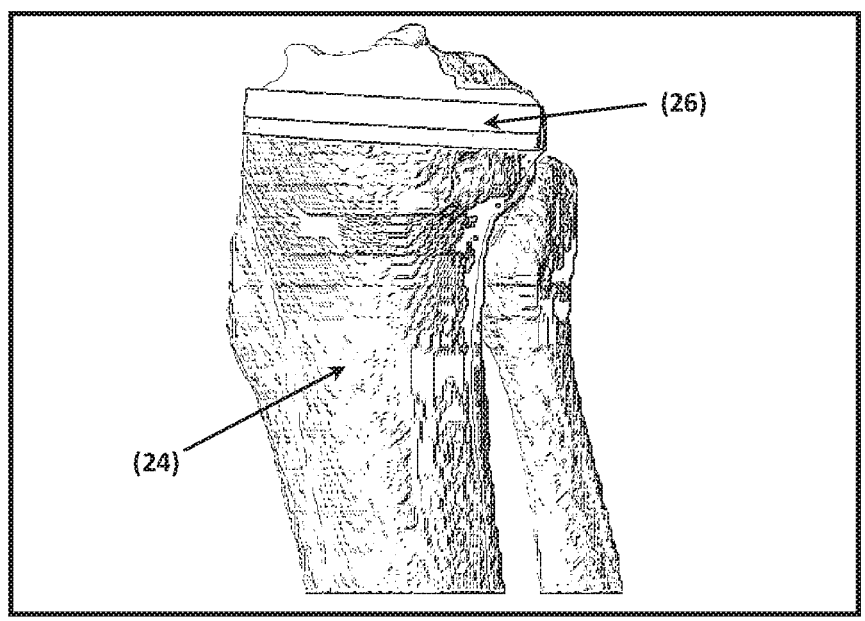
FIG. 13: shows side view of the tibial component (prosthesis) (26) over the tibia bone (24).
Figure 14:
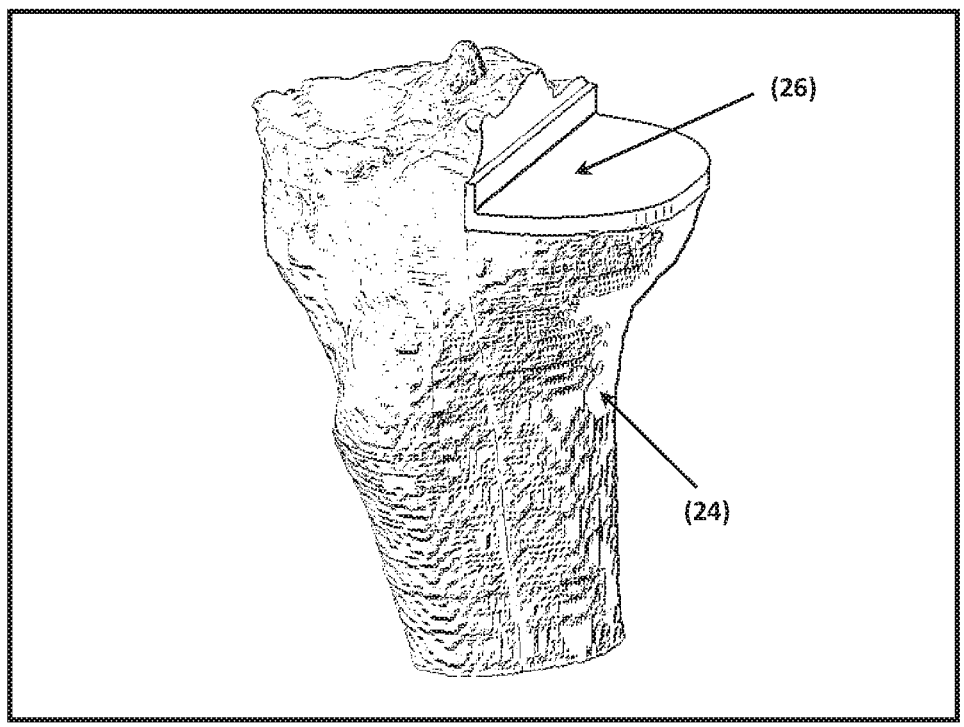
FIG. 14: shows isometric view of the tibial component (prosthesis) (26) over the tibia bone (24).
Figure 15:
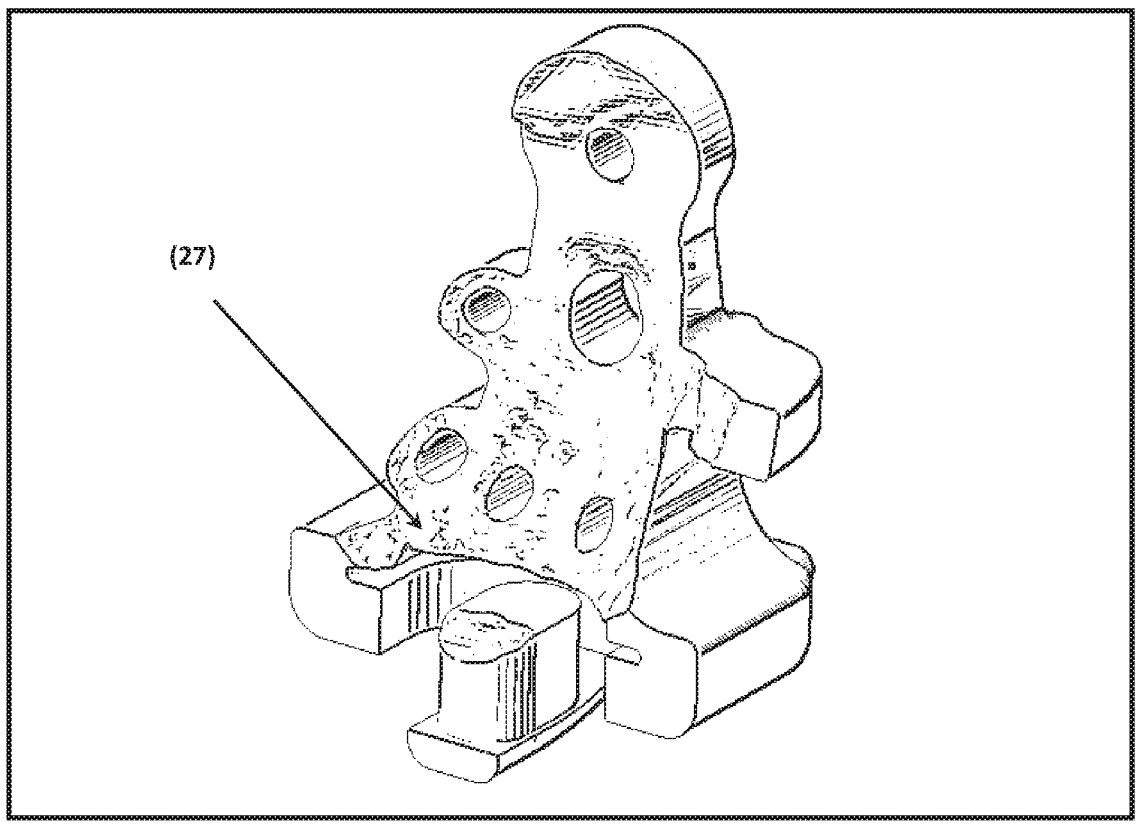
FIG. 15: shows isometric view of the femoral template after subtraction process.
Figure 16:
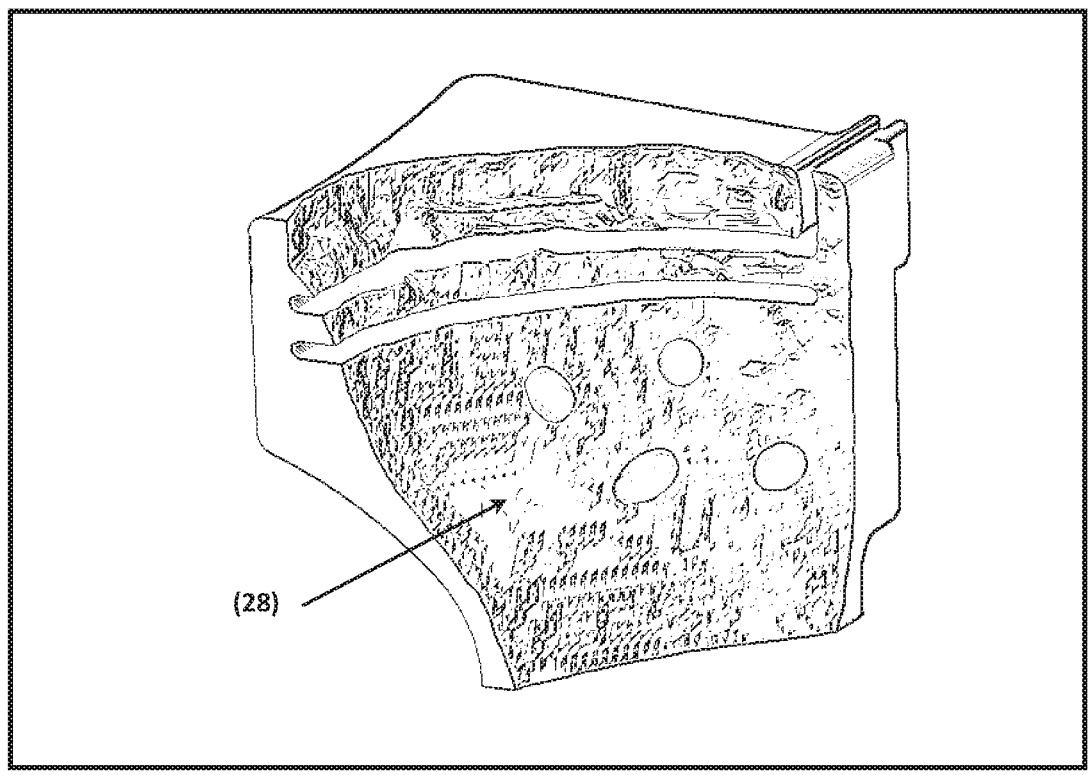
FIG. 16: shows isometric view of the tibial template after subtraction process.

The invention claimed is:

1. A device in the form of a patient specific instrument for performing cuts on a tibia bone and a femur bone during a uni-compartmental knee arthroplasty (UKA) based on preoperative planning for an implant and 3D imaging, the device comprising a femoral part and a tibial part, the tibial part having a vertical cutting slot and horizontal cutting slots with extensions linked together to the vertical cutting slot to maintain a complete removal of a portion of the tibia bone without the need for additional cuts, the tibial part adapted to seat on an anteromedial side of the tibia bone to avoid contact with the cartilage area on both a tibial plateau and a lateral side of the tibia bone to allow for a minimally invasive surgery to be performed.

2. The device in claim 1, wherein the device is adapted to be used for mobile and fixed bearing implants.

3. The device in claim 1, wherein said femoral part includes a cutting slot configured to perform a posterior cut on the femur bone.

4. The device in claim 1, wherein said femoral part includes drilling holes configured to form main holes for said implant on the tibia bone.

5. The device in claim 1, wherein said femoral part includes fixation holes with different diameters.

6. The device in claim 1, wherein said femoral part includes locating arms configured to match with a surface of the femur bone.

7. The device in claim 1, wherein the vertical cutting slot is configured to perform a vertical tibial cut on the tibia bone.

8. The device in claim 1, wherein a first horizontal cutting slot is configured to perform a horizontal tibial cut on the tibia bone; wherein a second horizontal cutting slot is configured to perform extra bone removal if needed.

9. The device in claim 1, wherein said tibial part includes fixation holes in oblique and parallel directions configured to drill fixation holes on said tibia bone to fix the device on the tibia bone.

10. The device in claim 1, wherein the extensions are configured to guide the cuts in the correct slope and inclination.

11. The device in claim 1, wherein the device is configured based on the 2D data of the implant.

* * * * *